United States Patent [19]

Middleman et al.

[11] Patent Number: 5,231,989

[45] Date of Patent: Aug. 3, 1993

[54] STEERABLE CANNULA

[75] Inventors: Lee M. Middleman, Portola Valley; Walter R. Pyka, Redwood City, both of Calif.

[73] Assignee: Raychem Corporation, Menlo Park, Calif.

[21] Appl. No.: 656,261

[22] Filed: Feb. 15, 1991

[51] Int. Cl.$^5$ .............................................. A61B 6/00
[52] U.S. Cl. ..................................... 128/657; 604/95; 604/280; 128/772; 128/4
[58] Field of Search ................... 604/95, 96, 264, 280, 604/281, 164, 170; 606/108, 78; 128/657, 772, 45 M, 4-6

[56] References Cited

U.S. PATENT DOCUMENTS

| | | | |
|---|---|---|---|
| 3,348,548 | 10/1967 | Chardack | 128/418 |
| 3,416,531 | 12/1968 | Edwards | 128/348 |
| 3,419,010 | 12/1968 | Williamson | 125/350 |
| 3,500,820 | 3/1970 | Almen | . |
| 3,516,412 | 6/1970 | Ackerman | 128/418 |
| 3,539,034 | 11/1970 | Tafeen | 128/221 |
| 3,729,008 | 4/1973 | Berkovits | 128/418 |
| 3,890,977 | 6/1975 | Wilson | 128/418 |
| 3,943,932 | 3/1976 | Woo | 128/303.18 |
| 4,033,331 | 7/1977 | Guss et al. | 128/2 M |
| 4,149,911 | 4/1979 | Clabburn | 148/11.5 R |
| 4,205,293 | 5/1980 | Melton et al. | 337/140 |
| 4,212,304 | 7/1980 | Finney | 128/349 |
| 4,307,723 | 12/1981 | Finney | 128/349 R |
| 4,378,811 | 4/1983 | Levitan | 128/757 |
| 4,401,433 | 8/1983 | Luther | 604/159 |
| 4,411,655 | 10/1983 | Schreck | 604/165 |

(List continued on next page.)

FOREIGN PATENT DOCUMENTS 0073308 6/1982 European Pat. Off. .
0079486 10/1982 European Pat. Off. .
0102685 5/1983 European Pat. Off. .
141006 1/1984 European Pat. Off. .

(List continued on next page.)

OTHER PUBLICATIONS

Japanese Patent Appln. No. 63-81727 (S. Shomi); Shape Memory and Superelasticity Effects in NiTi Alloys (Suzuki); Shape Memory Alloys (Schetky).
Variation in the Shape Reco-ery Temperature in Ni-Ti Alloys (Ling, et al.); and Kinzoku (Metal) (Kinzoku).
Baumgart, et al, "Memory Alloys-Properties, Phenomemological Theory and Applications," *Tech. Mitt. Krupp-Forsch-Ber.*, vol. 34, pp. 1-16, 1976.
Bensmann, et al., "Study of the Memory Alloy Nickel-Titanium and Observations on its Application in the Field of Medicine," *Tech. Mitt. Krupp-Forsch-Ber.*, vol. 37, pp. 21-34, 1979.
Buehler, et al., "55-Nitinol Unique Wire Alloy with a Memory," *Wire Journal*, Jun., 1963, pp. 41-49.
Cragg, et al, "Nonsurgical Placement of Arterial Endoprostheses: A New Technique Using Nitinol Wire," *Radiology*, Apr., 1983, vol. 147, pp. 261-263.
Dotter, et al., "Transluminal Expandable Nitinol Coil Stent Grafting: Preliminary Report," *Radiology*, Apr. 1983, vol. 147, pp. 259-260.
Otsuka, et al., "Shape-memory Alloys," *Metals Forum*, vol. 4, No. 3, 1981, pp. 142-152.
Portsmann, et al., "P Wave Synchronous Pacing Using Anchored Atrial Electrode Implanted without Thoracotomy," *The American Journal of Cardiology*, vol. 30, pp. 74-76, Jul., 1972.
Schetsky, L. M., "Shape-memory Alloys," *Scientific America*, Nov., 1979, pp. 74-82.

*Primary Examiner*—John D. Yasko
*Assistant Examiner*—C. Smith
*Attorney, Agent, or Firm*—Herbert G. Burkard

[57] ABSTRACT

A device suitable for insertion into a mammalian body comprises an elongated tube or cannula, an elastic member for bending the cannula, and a straightener preventing the elastic member from bending the cannula. The straightener and elastic member are capable of relative axial movement, so that the straightener can be positioned to prevent or allow the elastic from bending the cannula. Preferably the elastic member is formed from a superelastic shape-memory alloy. Other versions of the device without a straightener are described.

16 Claims, 17 Drawing Sheets

U.S. PATENT DOCUMENTS

| | | | |
|---|---|---|---|
| 4,616,656 | 10/1986 | Nicholson et al. | 128/630 |
| 4,650,467 | 3/1987 | Bonello et al. | 604/95 |
| 4,665,906 | 5/1987 | Jervis | 128/92 |
| 4,676,249 | 6/1987 | Arenas et al. | 128/657 |
| 4,742,817 | 5/1988 | Kawashima | 128/4 |
| 4,753,223 | 8/1988 | Bremer | 128/4 |
| 4,758,222 | 7/1988 | McCoy | 604/95 |
| 4,776,844 | 10/1988 | Ueda | 604/95 |
| 4,799,474 | 1/1989 | Ueda | 128/4 |
| 4,873,983 | 10/1989 | Winters | 128/657 |
| 4,895,168 | 1/1990 | Machek | 128/657 |
| 4,898,156 | 2/1990 | Gatturna et al. | 606/72 |
| 4,984,581 | 1/1991 | Stice | 128/772 |
| 5,025,799 | 6/1991 | Wilson | 128/657 |
| 5,040,543 | 8/1991 | Badera et al. | 128/772 |
| 4,425,908 | 1/1984 | Simon | 128/1 R |
| 4,427,000 | 1/1984 | Ueda | 128/6 |
| 4,452,236 | 6/1984 | Utsugi | 128/4 |
| 4,494,531 | 1/1985 | Gianturco | 128/1 R |
| 4,505,767 | 3/1985 | Quin | 148/402 |
| 4,509,517 | 4/1985 | Zibelin | 128/319 |
| 4,512,338 | 4/1985 | Balko et al. | 128/1 R |
| 4,543,090 | 9/1985 | McCoy | 604/95 |
| 4,556,050 | 12/1985 | Hodgson et al. | 128/1 R |
| 4,586,335 | 5/1986 | Hosoda et al. | 60/528 |
| 4,601,283 | 7/1986 | Chikama | 128/4 |
| 4,601,705 | 7/1986 | McCoy | 604/95 |

FOREIGN PATENT DOCUMENTS

| | | | |
|---|---|---|---|
| 132344 | 7/1984 | European Pat. Off. | |
| 140621 | 10/1984 | European Pat. Off. | |
| 0145166 | 10/1984 | European Pat. Off. | 128/657 |
| 167735 | 4/1985 | European Pat. Off. | |
| 279316 | 2/1988 | European Pat. Off. | |
| 330712 | 3/1988 | European Pat. Off. | |
| 0310295 | 4/1989 | European Pat. Off. | 604/96 |
| 1491628 | 11/1972 | Fed. Rep. of Germany | |
| 2802571 | 12/1978 | Fed. Rep. of Germany | |
| 3707899 | 9/1987 | Fed. Rep. of Germany | |
| 58-25140 | 2/1983 | Japan | |
| 58-29443 | 2/1983 | Japan | |
| 58-133225 | 8/1983 | Japan | |
| 59-97115 | 6/1984 | Japan | |
| 60-221718 | 11/1985 | Japan | |
| 62-20827 | 5/1987 | Japan | |
| 64-76824 | 3/1989 | Japan | |
| 64-85630 | 3/1989 | Japan | |
| 1-124473 | 5/1989 | Japan | |
| 1-135363 | 5/1989 | Japan | |
| 180101 | 5/1989 | Japan | |
| 1-164349 | 6/1989 | Japan | |
| 195901 | 6/1989 | Japan | |
| 1-170474 | 7/1989 | Japan | |
| 1-170475 | 7/1989 | Japan | |
| 1-181838 | 7/1989 | Japan | |
| 1-198563 | 8/1989 | Japan | |
| 1-198564 | 8/1989 | Japan | |
| 1-262372 | 10/1989 | Japan | |
| 1-262834 | 10/1989 | Japan | |
| 2-3740 | 1/1990 | Japan | |
| 2-19908 | 1/1990 | Japan | |
| 8301575 | 5/1983 | PCT Int'l Appl. | |
| 8902762 | 4/1989 | PCT Int'l Appl. | |
| 8906985 | 8/1989 | PCT Int'l Appl. | |
| 8902281 | 3/1989 | World Int. Prop. O. | 604/96 |

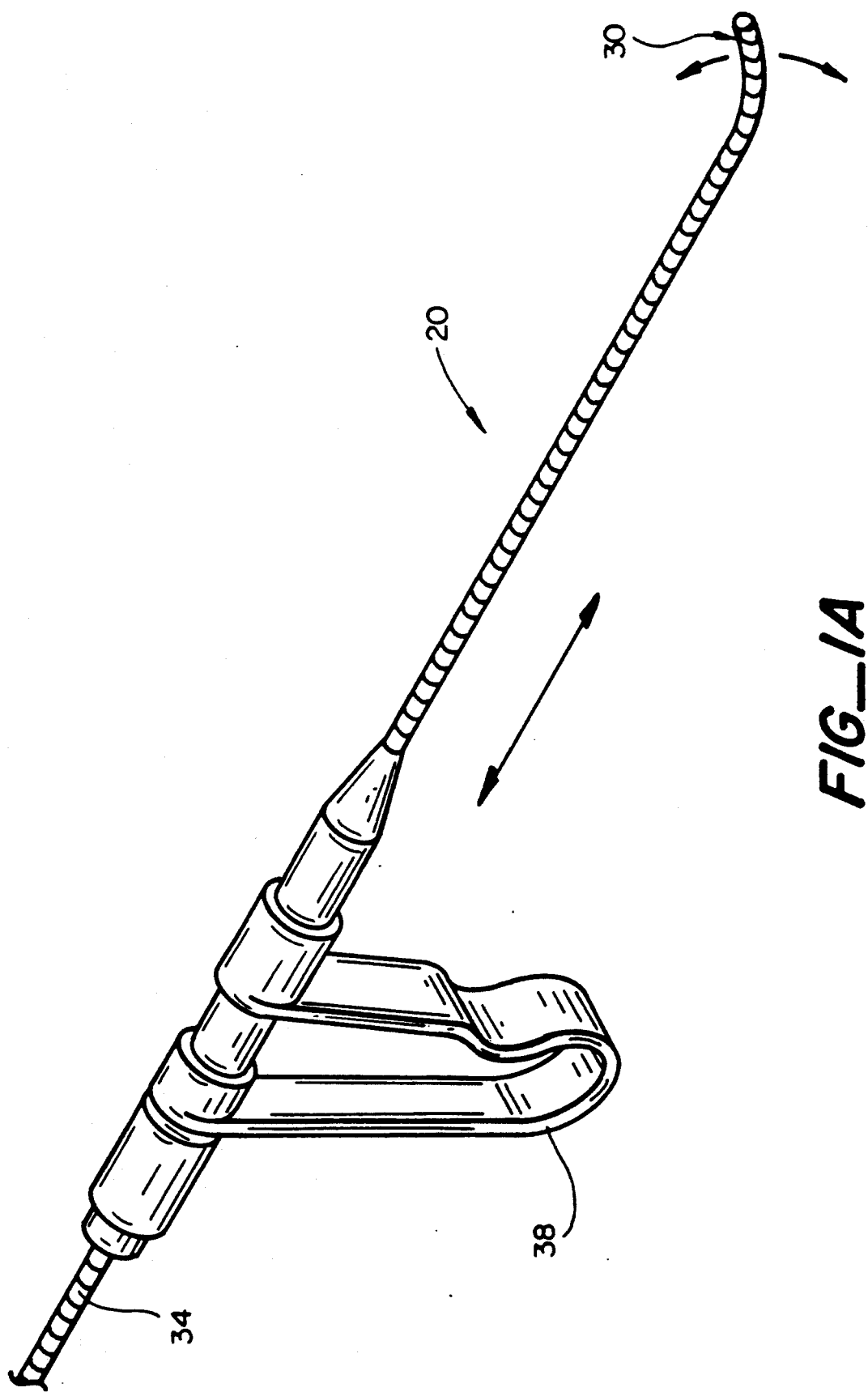
FIG_1A

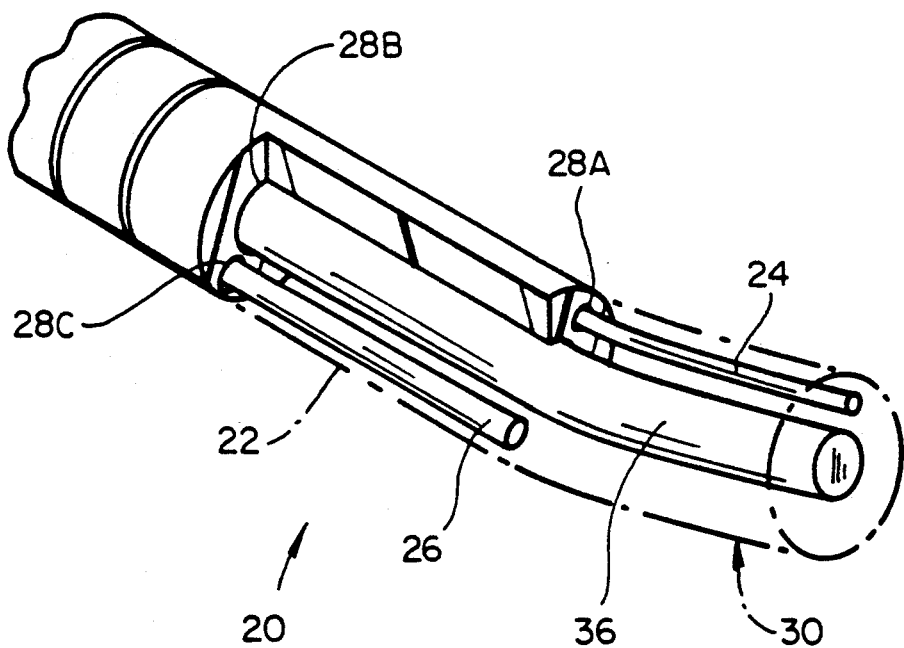
FIG_1B
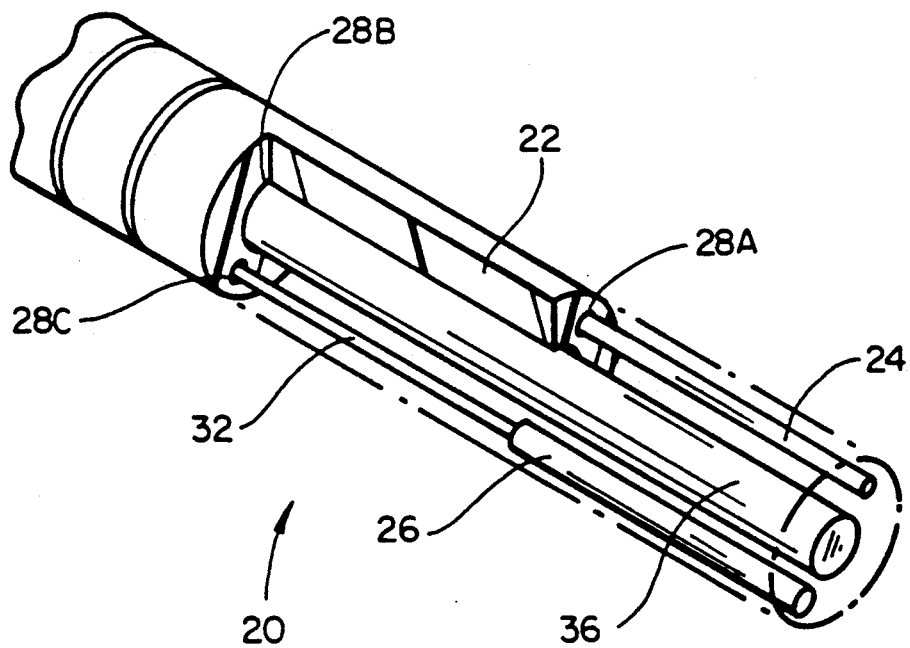
FIG_1C

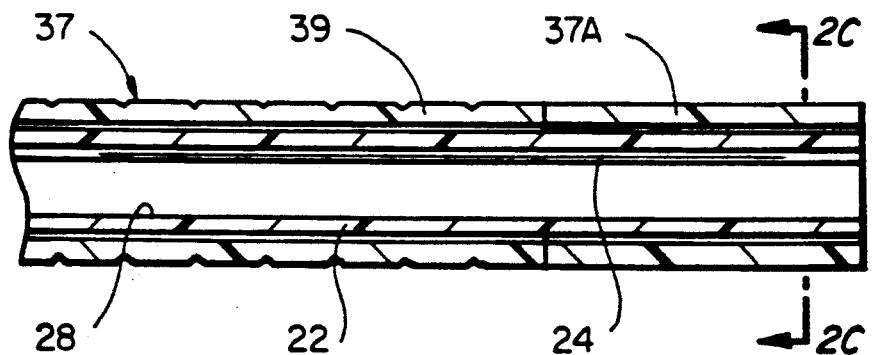
FIG_2A
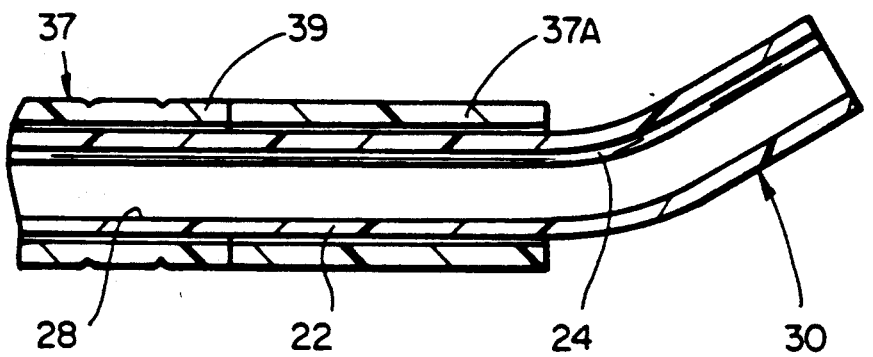
FIG_2B
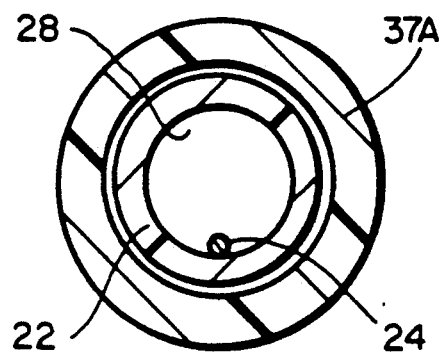
FIG_2C

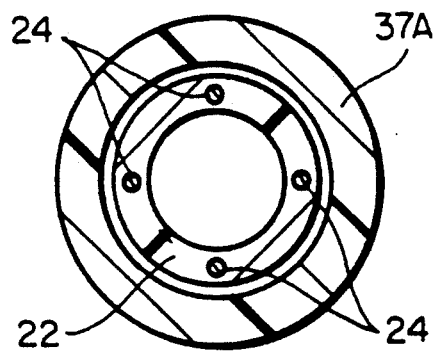
FIG_2D
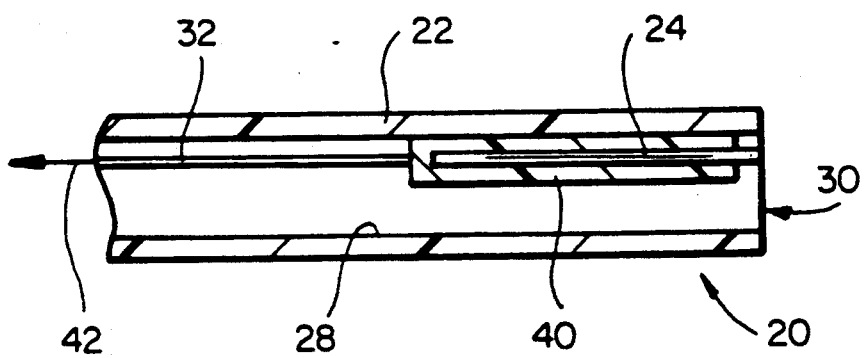
FIG_3A
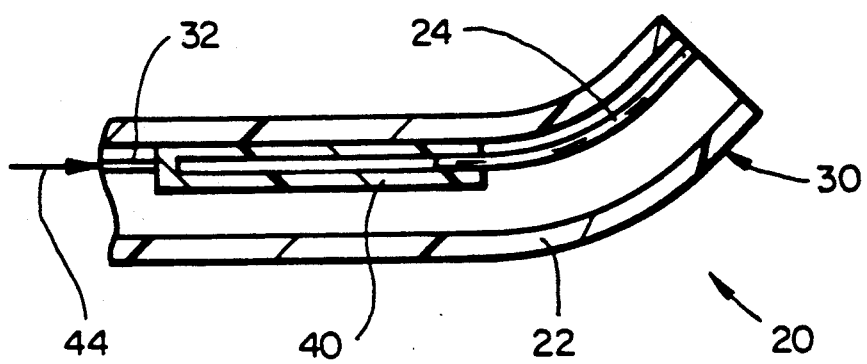
FIG_3B

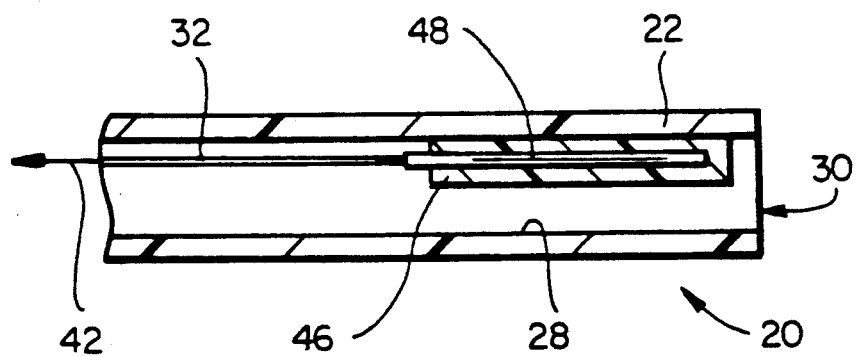
FIG_4A
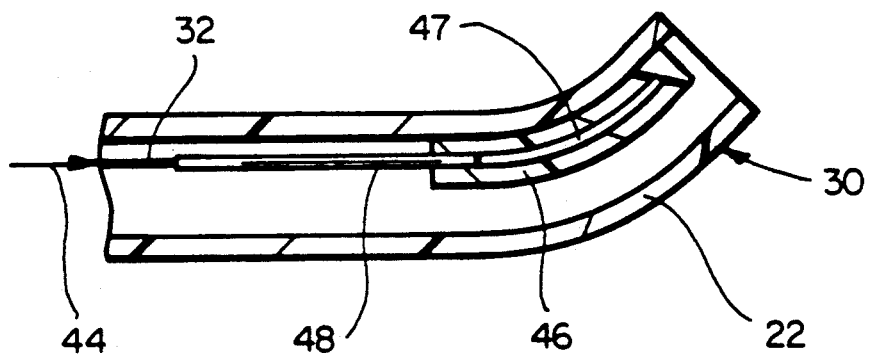
FIG_4B
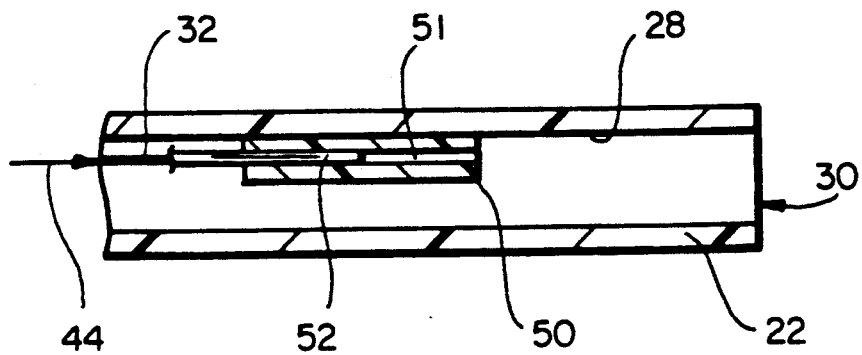
FIG_5A

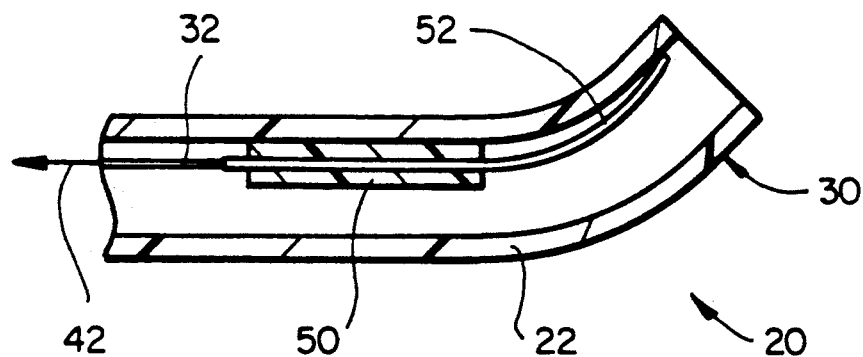
FIG_5B
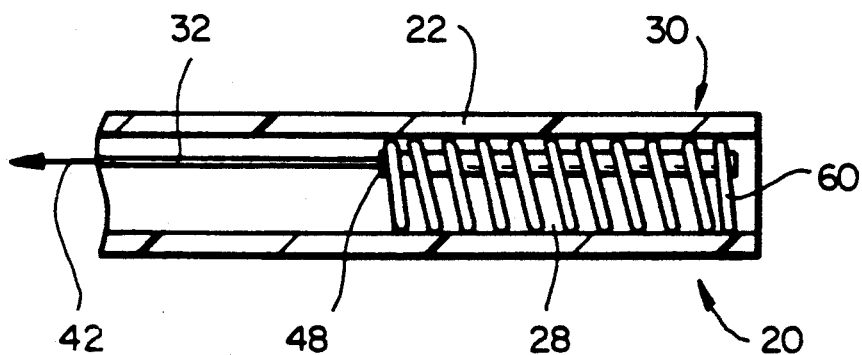
FIG_6A
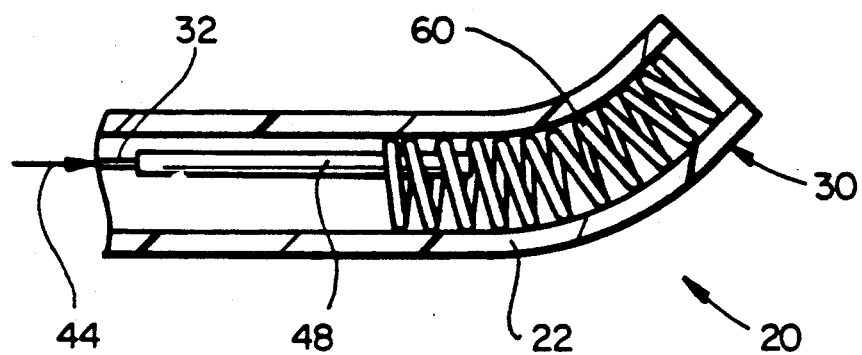
FIG_6B

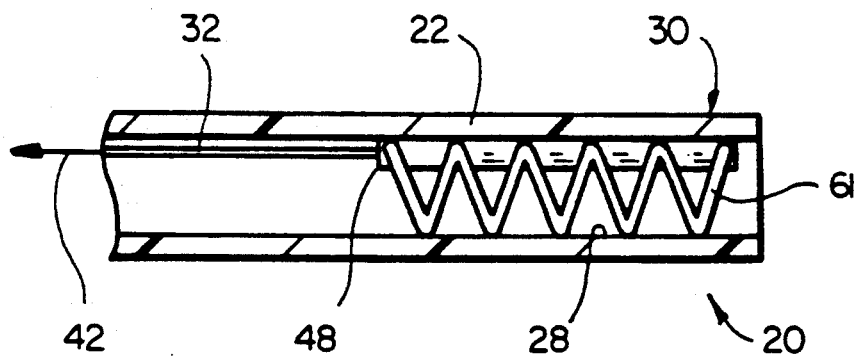
FIG_7A
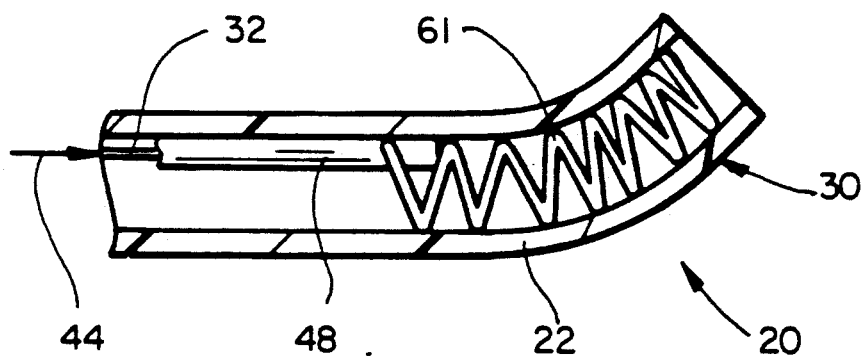
FIG_7B
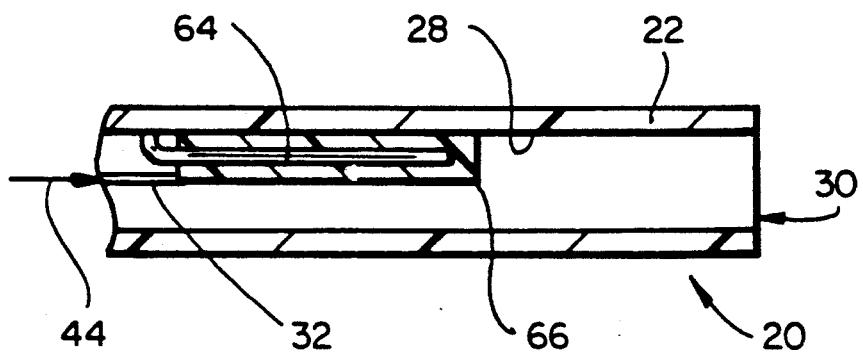
FIG_8A

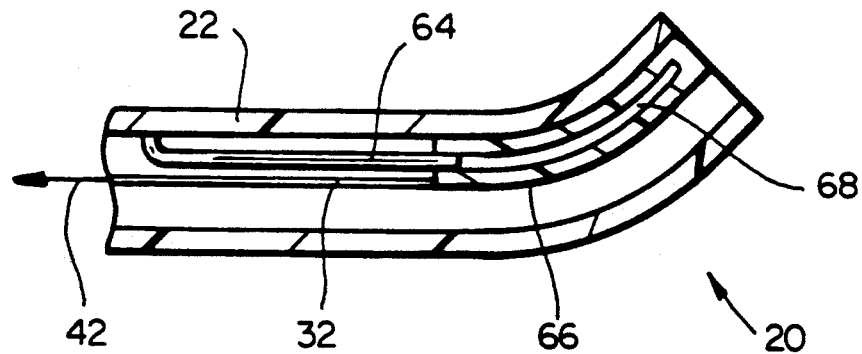
FIG_8B
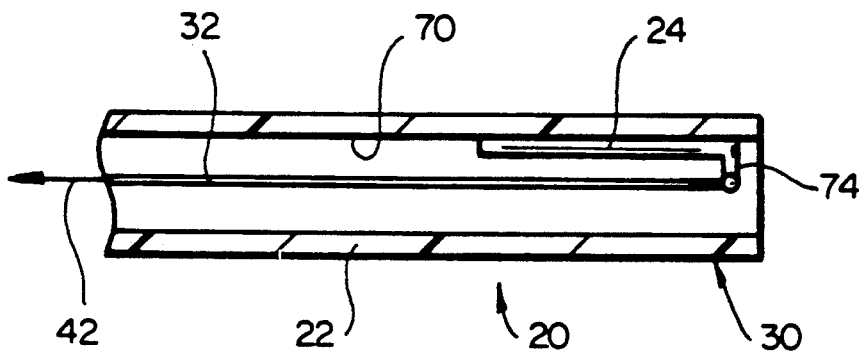
FIG_9A
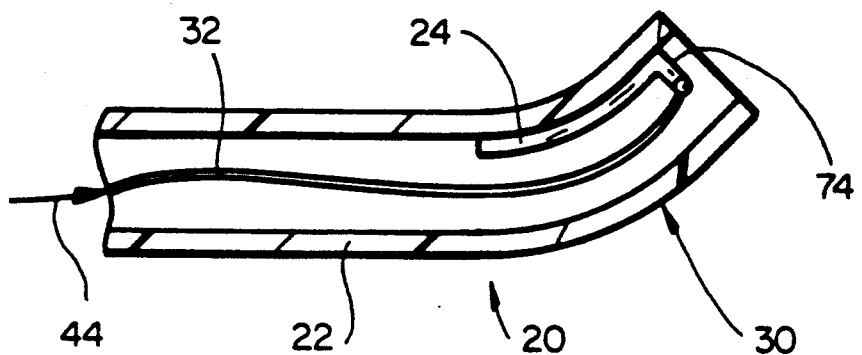
FIG_9B

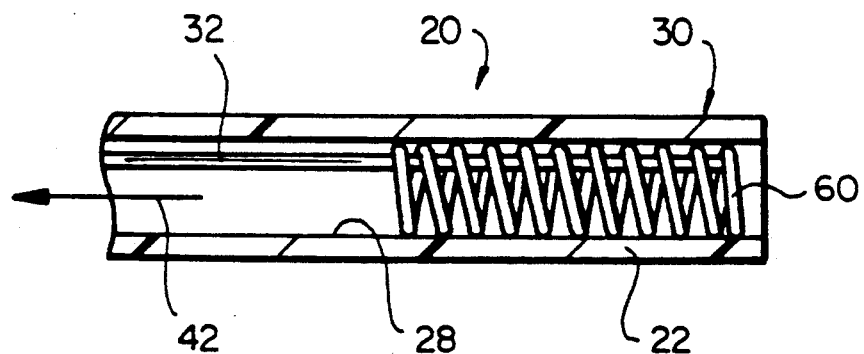
FIG_10A
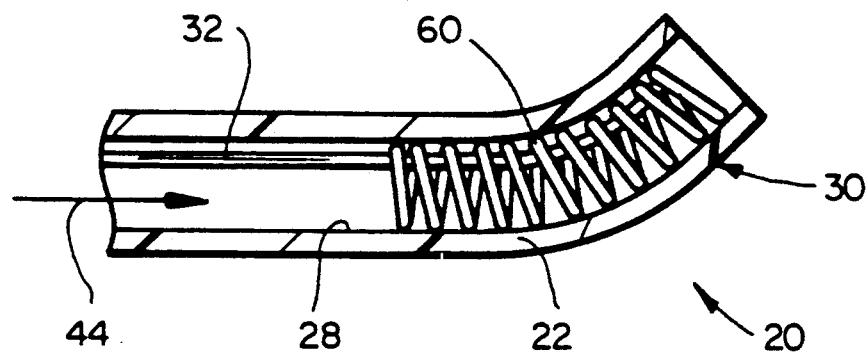
FIG_10B
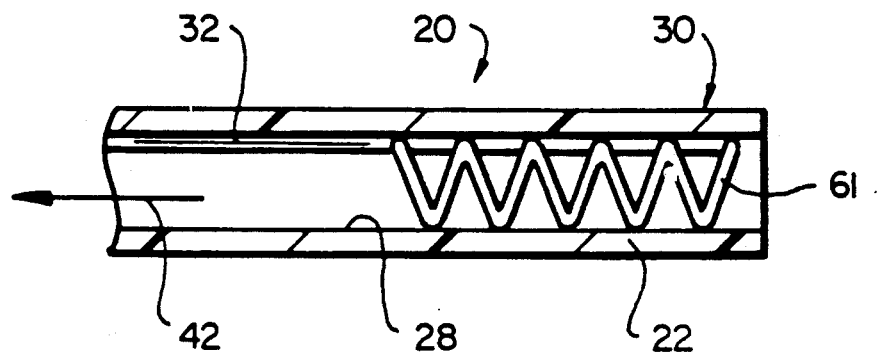
FIG_11A

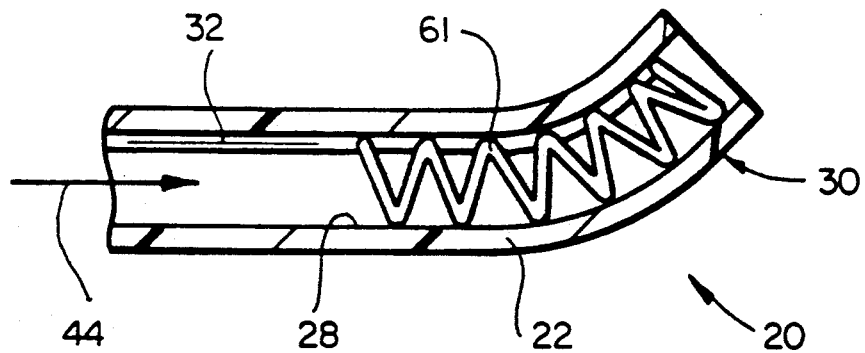
FIG_11B
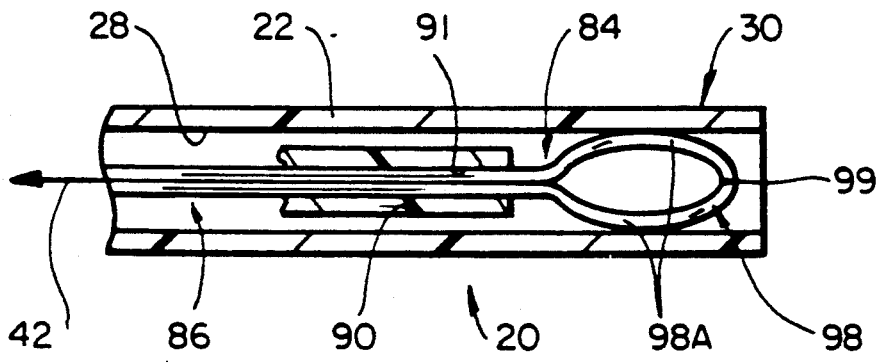
FIG_12A-1
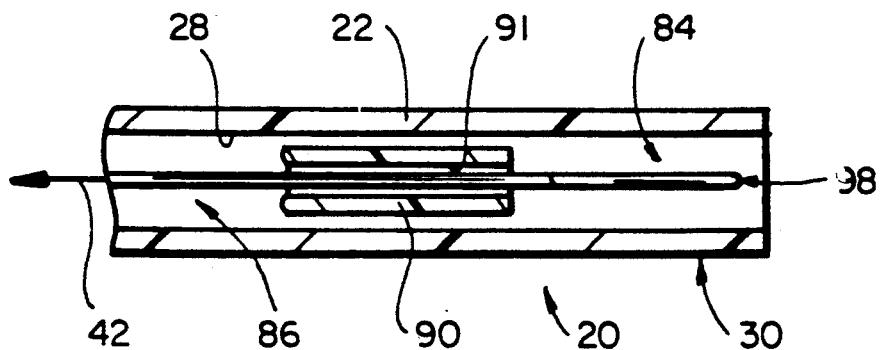
FIG_12A-2

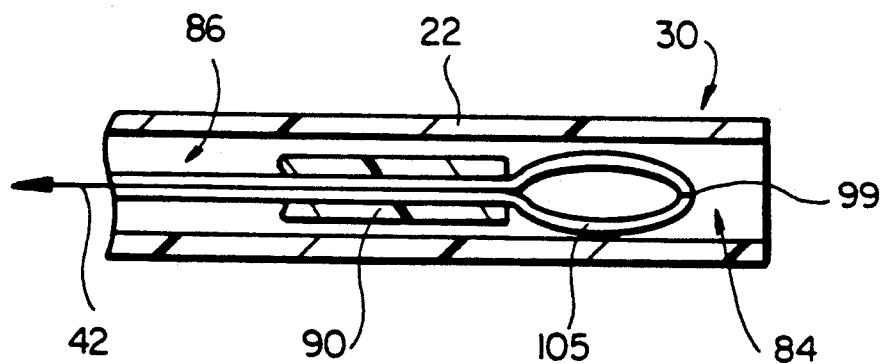
FIG_12B-1
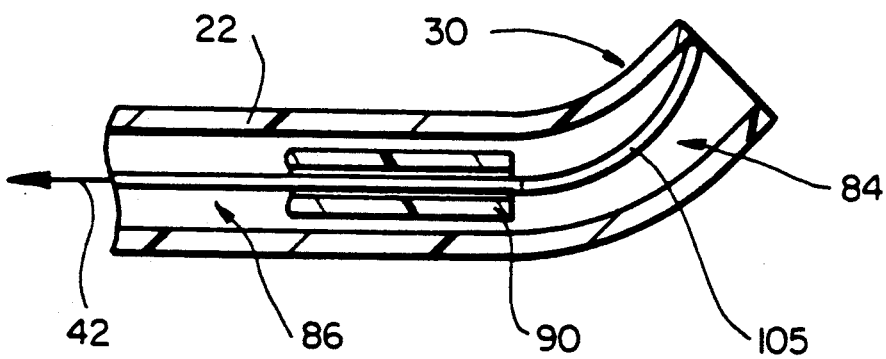
FIG_12B-2
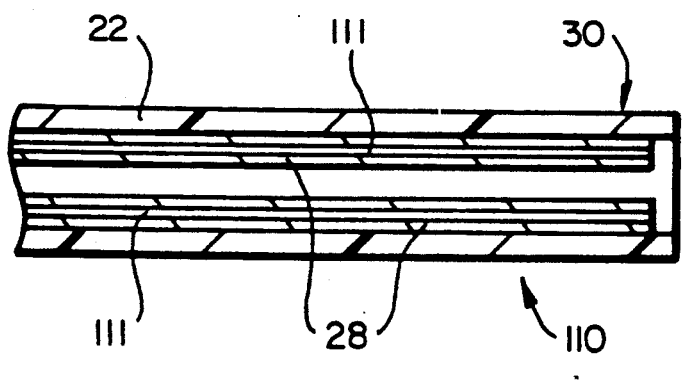
FIG_13A

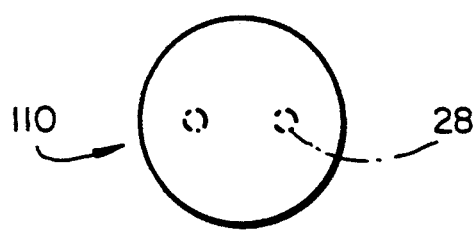
FIG_13B-1
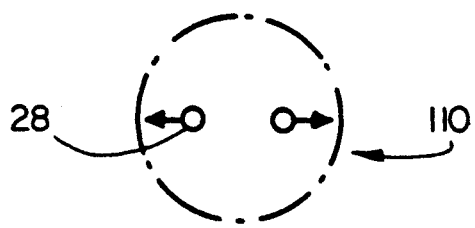
FIG_13B-2
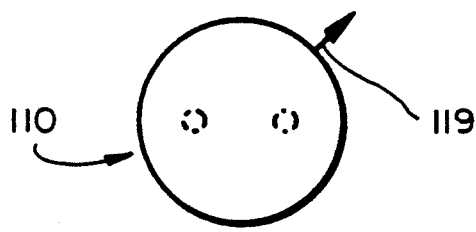
FIG_13C-1
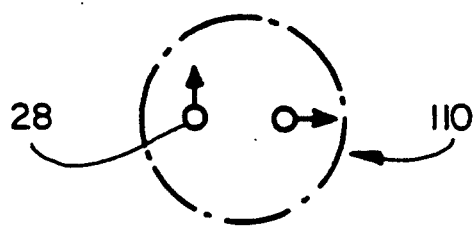
FIG_13C-2

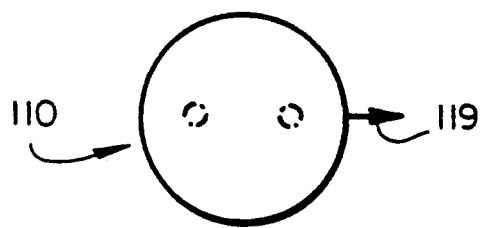
*FIG_13D-1*
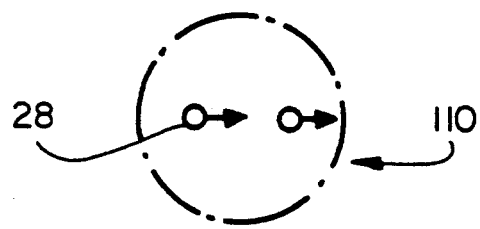
*FIG_13D-2*
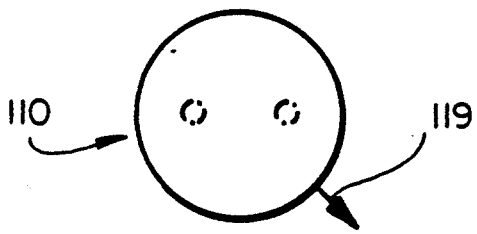
*FIG_13E-1*
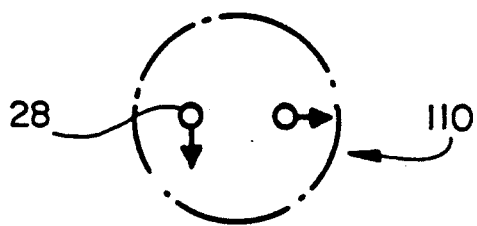
*FIG_13E-2*

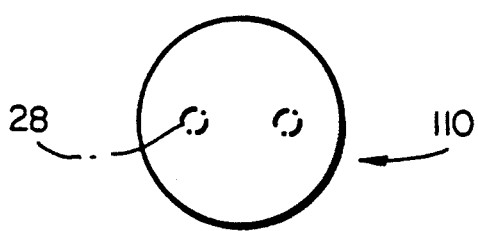
FIG_13F-1
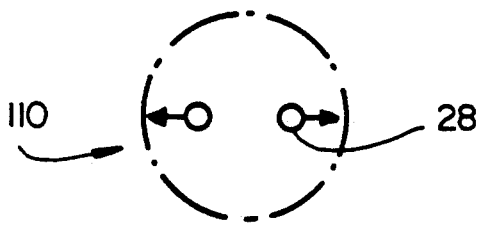
FIG_13F-2
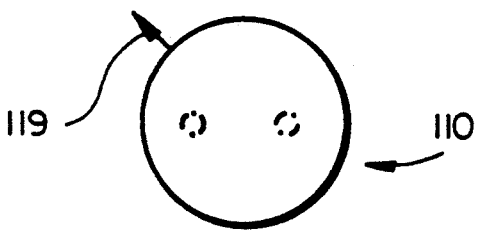
FIG_13G-1
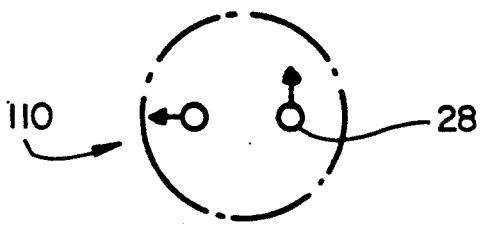
FIG_13G-2

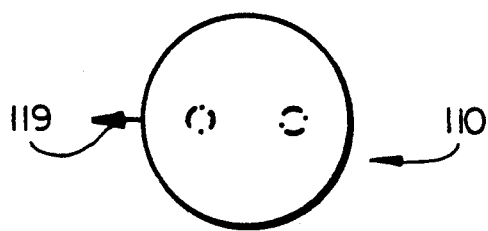
FIG_13H-1
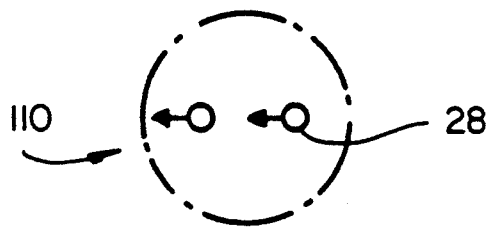
FIG_13H-2
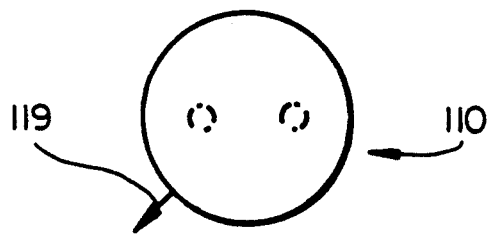
FIG_13I-1
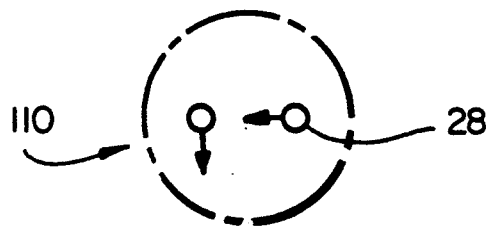
FIG_13I-2

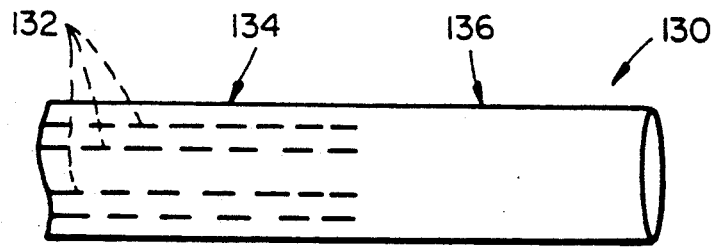
*FIG_14A*
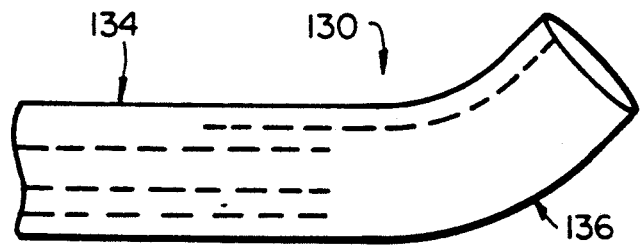
*FIG_14B*
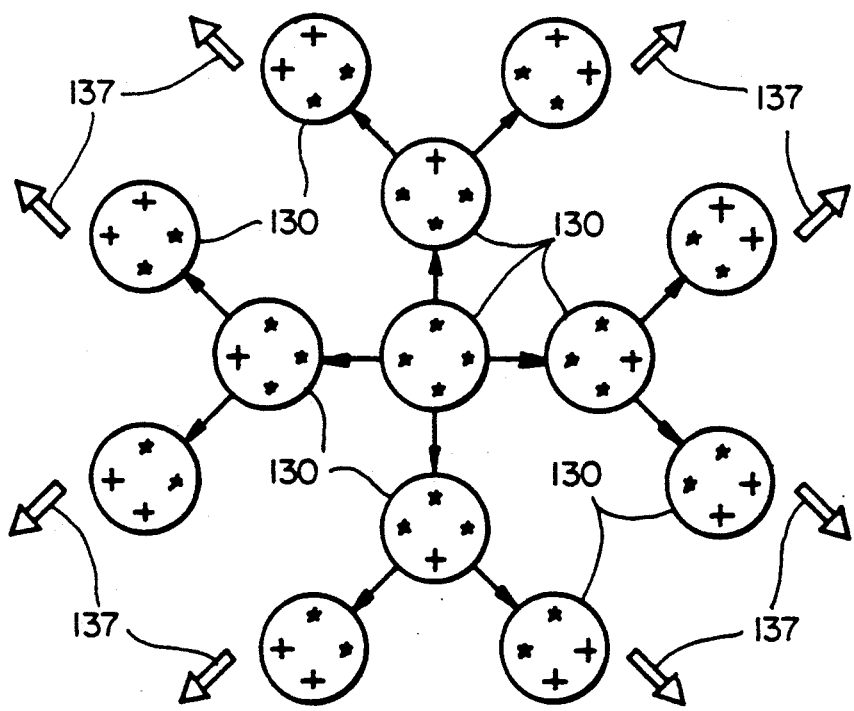
*FIG_14C*

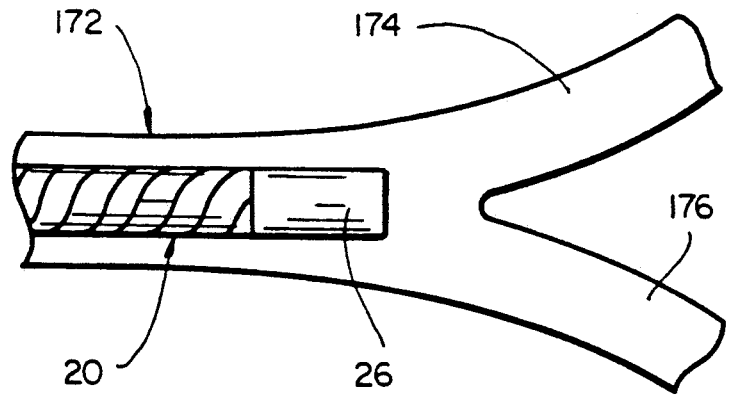
FIG_15A
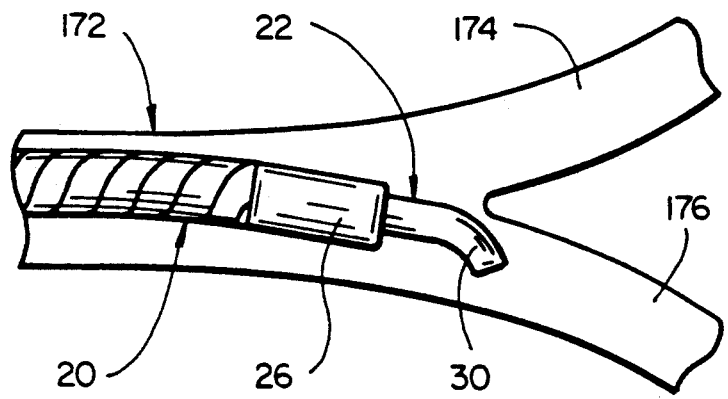
FIG_15B
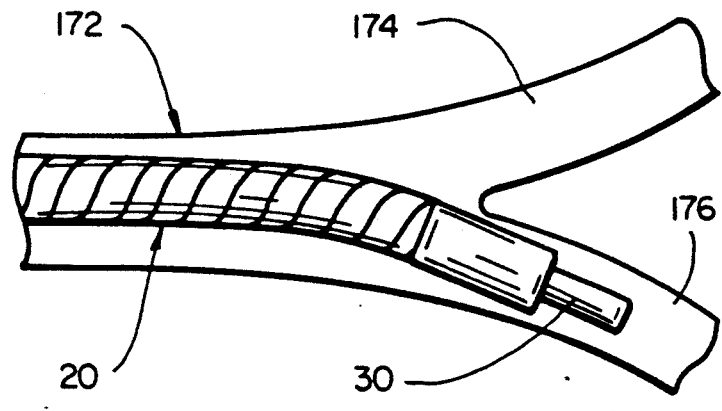
FIG_15C

STEERABLE CANNULA

BACKGROUND

The present invention relates to a device suitable for insertion into a mammalian body.

Cannula including catheters, stents, and the like have many medical applications. These devices are usually passed into and through a body orifice, incision, peripheral artery, vein, or urogenital tract of a mammalian body and advanced until they reach a desired organ, structure, or cavity within the body.

These devices are available in many forms and are used for a wide variety of purposes, including diagnostic and therapeutic purposes. Among the uses of these devices are the insertion of dyes and medicines into the body; stents such as for urinary or drainage tubes; endoscopes for viewing what is going on in the body; sampling body fluids; monitoring the electrical properties of body organs such as the heart; passageways for insertion of smaller diameter cannula or catheters; and therapeutic techniques such as angioplasty.

A problem experienced with cannulae is inserting them into the desired location without damaging body tissues or organs. A cannula needs to be sufficiently stiff that it can be guided into place, yet at the same time sufficiently soft so as not to damage or penetrate the body tissue. For example, insertion of a cannula into a coronary artery or the colon requires advancement along a tortuous, bent path with sensitive tissue along the path, and in the case of the vascular path, a path having a large number of branch points.

A variety of techniques have been developed to guide a cannula into a desired location. One such technique utilizes a guide wire comprising an elastic material such as a wire. The guide wire is used to negotiate a bent portion of an organ, such as a blood vessel, in advance of the flexible tube that is to be inserted. This is a time-consuming and tedious process.

Other devices have been developed using shape-memory alloys in a cannula. The shape of the shape-memory alloy and thus the cannula is changed upon heating of the alloy. Such a device is shown in U.S. Pat. No. 4,601,283. Other devices directed to insertion of a cannula into a mammalian body through a tortuous path are described in U.S. Pat. Nos. 3,539,034; 3,868,956; 3,890,977; 4,033,331; 4,427,000; 4,452,236; 4,665,906; 4,742,817; and 4,926,860.

Many of these devices suffer from one or more disadvantages, including excessive stiffness of the cannula, complexity of operation such as a need to heat a shape-memory alloy, and lack of adjustability over a wide range of curvatures while the tube is in a body channel.

SUMMARY

The present invention is directed to an article or device for insertion into a mammalian body that has none of these disadvantages and has many desirable features, namely:

a. sufficient steerability that it can navigate tortuous, branched paths through a mammalian body;

b. sufficient softness and flexibility that tissue and organs are not damaged or traumatized;

c. ease of use, with no external heating required; and d. ability to have the curvature adjusted over a large range even while the cannula is in a body channel.

The article comprises three main elements: (1) an elongated tube or cannula; (2) an elastic member for bending a hollow, bendable, distal segment of the cannula; and (3) straightening or stiffening means capable of preventing the elastic member from bending. The elastic member is capable of engaging the distal segment of the cannula without totally blocking the internal lumen (or lumina) of the cannula. The elastic member has two general configurations, a bent shape and a substantially straight shape. The elastic member is sufficiently stiff to cause the distal segment to bend when the elastic member is in its bent shape. The straightener is capable of preventing the elastic member from bending the distal segment of the cannula.

In one version of the invention, the straightener and the elastic member are capable of relative axial movement. The purpose of the movement is to transform the elastic member from one shape to another for correspondingly bending or unbending the distal segment of the tube. In a preferred version of the invention, the straightener prevents the elastic member from assuming its bent shape, thereby resulting in the cannula being substantially straight and linear. When the straightener is disengaged from the elastic member, the elastic member bends and thereby causes the distal segment of the cannula to bend.

The article typically includes an elongated wire or other means for causing relative axial movement between the straightener and the elastic member. The relative axial movement can be the result of the straightener moving relative to the elastic member or vice versa. For example, the elastic member can be secured to the cannula, with the straightener being tubular and on the outside of the cannula, and the cannula can be extruded out of the straightener to assume a curved configuration.

For ease of operation, preferably the elastic member is a memory alloy element formed at least partly from a shape-memory alloy, and most preferably formed at least partly from a pseudoelastic, and most preferably, a superelastic shape-memory alloy that displays reversible stress-induced martensite at about body temperature. As stress is applied to the alloy, the martensite content of the alloy decreases (and the austenitic content decreases), and as stress is removed from the alloy, the austenite content increases (and the martensite decreases). For convenience, the former state is referred to as the "stress-induced martensitic state" and the latter state is referred to as the "austenitic state". However, it is unlikely that the alloy is ever 100% martensite in its stress-induced martensitic state or 100% austenite in its austenitic state at operating temperatures.

The memory alloy element is in its bent shape when the alloy is in either its stress-induced martensitic state or austenitic state, and the memory alloy element is substantially straight when the alloy is in its opposite state.

A particular advantage of using a superelastic shape-memory alloy is that the elastic member can transform from one shape to another without any application of heat.

A variety of physical configurations are possible for this article. For example, the elastic member can be in the lumen of the cannula, exterior of the cannula, or built into the wall of the cannula. A plurality of elastic members can be used, and the elastic member can be linear, helical, zigzag, or tubular in shape.

The straightener can be tubular and around the peripheral wall of the cannula, or can be inside the cannula as a rod or tube. When the elastic member is tubular, the straightener can be inside the elastic member. When the straightener is tubular, the elastic member can be sized to fit inside the straightener. The elastic member can be incorporated into the peripheral wall of the cannula.

The article can be used for a variety of applications. For example, it can be used as an endoscope provided with multiple lumens for the various elements of an endoscope such as the light guide. The article can be used as a stent or for insertion of a therapeutic or diagnostic agent into a mammalian body.

A device according to the present invention has significant advantages. When the cannula is the external member, the device is sufficiently soft and flexible that tissue and organs are not damaged or traumatized. Through the use of an elastic member, sufficient steerability is obtained that the device can navigate the tortuous and branched paths found throughout a mammalian body. Further, the device is easy to use, with a change in curvature of the distal segment of the cannula being achieved merely by moving the straightener or the elastic member. No external heating is required, and by controlling the amount of movement of the straightener or elastic member, the bend of the device can be adjusted over a large range even while the cannula is in a body channel.

In another version of the invention, the straightener is replaced with a stressing element, the stressing element being attached to an elastic member made at least partly from a superelastic shape-memory alloy. Tensioning the stressing member results in the alloy being transformed to contain more stress-induced martensite and the elastic member assuming a substantially straight shape, thereby substantially straightening the distal segment of the cannula. Release of the tension on the stressing member results in transformation of the alloy to contain more austenite and the elastic member transforming into a bent shape for bending the distal segment of the cannula.

In another device according to the present invention, the purpose of the straightener is replicated by varying the diameter of the internal lumen of a cannula, or for example, by providing two cannula of different diameters. The device has a distal segment provided with a lumen of a relatively large diameter, and an adjoining less distal segment with a lumen of relatively small diameter. An elongated elastic member is provided inside the lumens and is axially slidable in the lumens. The elastic member comprises two segments connected to each other at their distal ends. The elastic segments are bowed at their distal ends, such that they form a loop-like structure, where the loop is substantially unstressed when it is completely inside the distal portion of the lumen. The unstressed loop is in a plane substantially parallel to the axis of the cannula. When the loop is withdrawn into the portion of the lumen which has a relatively small diameter, the bowed portions of the elastic segments are stressed. The stress tends to cause the bowed portions to fold together out of the plane parallel to the axis of the cannula, since the stress tends to create a bending stress at the connected tips of the segments, with some torsional stress in the tail parts of the segments.

Because the bowed parts of the segments are forced into a folded configuration which is generally perpendicular to the plane of the unstressed loop, the cannula bends in a direction generally perpendicular to the original plane of the loop. Complete withdrawal of the elastic segments into the portion of the lumen which has a relatively small diameter leaves the distal part of the cannula unsupported, which permits it to be straight, and also soft and flexible.

The straightener can also be an elastic member. For example, two elongated, rotatable, elastic or bending members can be placed in the lumen of a cannula, both elastic members acting to bend the cannula. By rotating one of the elastic relative to the other elastic members, the force exerted by the bending moments of the elastic members on the cannula can be varied. For example, if the bending moments are opposite each other, no bending occurs (and thus one of the elastic members serves as the straightener). If the bending moments are in the same direction, maximum bending occurs.

A similar effect can be achieved with a plurality of elastic or bending members axially slidable in the cannula, at least two of which exert bending moments on the distal segment of the cannula in different directions. By axially sliding an elastic member into the distal segment of the cannula, it exerts a bending moment on the distal segment. By sliding an additional elastic member into the distal segment, the direction of the bending of the distal segment and the amount of bending can be varied.

DRAWINGS

These and other features, aspects, and advantages of the present invention will become better understood with reference to the following description, appended claims, and accompanying drawings where:

FIG. 1A is a perspective view of an endoscope having features of the present invention;

FIGS. 1B and 1C are perspective views, partly in section, of the tip portion of the endoscope of FIG. 1A, the tip portion being in a curved configuration in FIG. 1B and in a straight configuration in FIG. 1C;

FIGS. 2A and 2B are longitudinal sectional views of an end portion of a cannula embodying features of the present invention, the cannula being in a straight configuration in FIG. 2A and in a curved configuration in FIG. 2B;

FIG. 2C is a transverse sectional view of the cannula portion of FIG. 2A taken along line 2C—2C in FIG. 2A;

FIG. 2D is a view similar to that of FIG. 2C of another version of a cannula having a multiplicity of elastic members;

FIGS. 3A and 3B are longitudinal sectional views of the portion of a second version of a cannula embodying features of the present invention, the end portion being in a straight configuration in FIG. 3A and in a curved configuration in FIG. 3B;

FIGS. 4A and 4B are longitudinal sectional views of the end portion of a third version of a cannula embodying features of the present invention, the end portion being in a straight configuration in FIG. 4A and in a curved configuration in FIG. 4B;

FIGS. 5A and 5B are longitudinal sectional views of the end portion of a fourth version of a cannula embodying features of the present invention, the end portion being in a straight configuration in FIG. 5A and in a curved configuration in FIG. 5B;

FIGS. 6A and 6B are longitudinal sectional views of the end portion of a fifth version of a cannula embodying features of the present invention, the end portion being in a straight configuration in FIG. 6A and in a curved configuration in FIG. 6B;

FIGS. 7A and 7B are longitudinal sectional views of the end portion of a sixth version of a cannula embodying features of the present invention, the end portion being in a straight configuration in FIG. 7A and in a curved configuration in FIG. 7B;

FIGS. 8A and 8B are longitudinal sectional views of the end portion of a seventh version of a cannula embodying features of the present invention, the end portion being in a straight configuration in FIG. 8A and in a curved configuration in FIG. 8B;

FIGS. 9A and 9B are longitudinal sectional views of the end portion of a eighth version of a cannula embodying features of the present invention, the end portion being in a straight configuration in FIG. 9A and in a curved configuration in FIG. 9B;

FIGS. 10A and 10B are longitudinal sectional views of the end portion of a ninth version of a cannula embodying features of the present invention, the end portion being in a straight configuration in FIG. 10A and in a curved configuration in FIG. 10B;

FIGS. 11A and 11B are longitudinal sectional views of the end portion of a tenth version of a cannula embodying features of the present invention, the end portion being in a straight configuration in FIG. 11A and in a curved configuration in FIG. 11B;

FIGS. 12A-1 and 12B-1 are partial longitudinal sectional views of the end portion of an eleventh version of a device embodying features of the present invention, the device having two joined superelastic elements, with the superelastic elements extending out of a small diameter lumen in FIG. 12A-1, and partially withdrawn into a small diameter lumen in FIG. 12B-1;

FIGS. 12A-2 and 12B-2 correspond to FIGS. 12A- and 13B-1, respectively, the version "2" Figures being side partial longitudinal sectional views;

FIG. 13A schematically shows an end portion of a twelfth version of a device according to the present invention where two rotatable elastic members are in the lumen of a cannula;

FIGS. 13B-13I show the net bending moments on the cannula of FIG. 13A resulting from rotating one of the elastic members relative to the other;

FIGS. 14A and 14B schematically show an end portion of a thirteenth device according to the present invention having four elastic members axially slidable in a cannula, and FIG. 14C schematically shows the net effective bending moment on the cannula depending on which of the elastic members is engaging the distal portion of the cannula; and FIGS. 15A, 15B, and 15C are schematic views showing a cannula according to the present invention advancing beyond a branch point in a body fluid system.

DESCRIPTION

An article 20 having features of the present invention, as shown in FIGS. 1A, 1B and 1C, comprises as its main elements an elongated tube or cannula 22, an elastic member 24, and a straightener or stiffener 26. The cannula 22 has at least one internal lumen 28. The elastic member 24 has a substantially straight shape as shown in FIG. 1C, and a bent shape as shown in FIG. 1B. The elastic member is sufficiently stiff to cause a pliable and bendable distal segment 30 of the cannula to bend when the elastic member 24 is in its bent shape. The straightener 26 is sufficiently stiff to prevent the elastic member 24 and the cannula 22 from bending when the straightener 26 is located in the distal segment 30 of the cannula 22.

The straightener 26 is moved axially within the lumen 28 with a draw wire 32. Pulling the draw wire 32 towards the proximal end 34 of the article 20 to the position shown in FIG. 1B results in bending of the distal segment of the cannula. Pushing on the draw wire 32 to move the straightener 26 into the distal segment 30 of the cannula 22 straightens the cannula so that it assumes the shape shown in FIG. 1C.

As described in detail below, although the device 20 shown in FIG. 1 is adapted to be used as an endoscope, devices according to the present invention have many uses and applications. Such a device can be used for substantially any application where a cannula is currently used for treatment of a mammal, particularly humans. For example, such a device can be used for electrical monitoring, drainage, pressure reading, gas administration, insertion of medication, insertion of dyes, withdrawal of tissue or fluid samples, and introduction of other devices such as angioplasty catheters or forceps. The device can be used for a wide variety of body parts including the cardiovascular, urogenital, respiratory, lymph, and digestive systems.

Among specific applications of a device according to the present invention are use as an endoscope as described in U.S. Pat. No. 4,427,000; an intraperitoneal catheter as described in German Patent DE3147722A1; a suprapubic catheter as described in Canadian Patent 1,001,034; and a plastic tube for sinusitis conditions as described in European Patent Application 0129634.

Applications for a device according to the present invention are not limited to medical applications, but include other applications for industry and research, such as viewing or repairing difficult to reach locations. These include dangerous locations such as facilities contaminated with radiation.

The present invention will be described with reference to use of a cannula 22. The term "cannula" includes any elongated, hollow tubular device, including catheters and stents. The cannula can have a distal end that is either open or closed.

The cannula 22 can be formed from a wide variety of materials. It is generally a polymeric material such as polyethylene, polyvinyl chloride, polyester, polypropylene, polyamide, polyurethane, polystyrene, fluorine plastics and silicone rubber, or an elastomer or a composite material of the above-mentioned plastics, to thereby form a soft, smooth surface with no irregularities thereon. In addition, the cannula can comprise an anti-coagulating agent such as heparin and urokinase, or a coating of an anti-thrombus material such as silicone rubber, a block copolymer of urethane and silicone (®Avcothane), a copolymer of hydroxylethyl methacrylate-styrene and the like, and can obtain low friction properties by use of resin having a low frictional surface such as fluoro resin and through applying a lubricant such as silicone oil. Furthermore, an X-ray contrast medium comprising a metal such as Ba, W, Bi, Pb or the like, or a compound therebetween can be mixed with the synthetic resin material forming the cannula, so that the position of the cannula in a vessel can be accurately determined roentgenographically within a body.

The straightener 26, which serves as a restraining collar in FIG. 1, can be formed of most metallic materials such as surgical stainless steel, and most polymeric materials. It can be formed of the same material as the cannula, but must have more rigidity, such as by being filled with a filler, to resist the bending force of the elastic member 24. The straightener 26 can be a separate element attached to the draw wire 32, or it can be a coating over or a filling in the distal part of the draw wire 32.

Only a portion of the straightener element 26 needs to have sufficient stiffness and rigidity to resist the bending force of the elastic member 24. It is not necessary that the entire straightener 26 be stiff. For example, the straightener can be a collar that is around the exterior of the cannula, with only the portion of the straightener proximate to the elastic member 24 formed of a stiff material. The rest of the straightener can be as flexible as the cannula.

The straightener can be essentially any shape, such as a wire, rod, strip, or tubular, and can be elongated or short. The minimal length of the straightener is about the same as the length of the distal segment 30 that the straightener is designed to prevent from bending, typically from about 1 to about 50 cm in length.

The elastic member 24 is formed from an elastic material that displays flexible, resilient memory properties. The term "elastic material" is used herein to mean a material that has springlike properties, that is, it is capable of being deformed by an applied stress and then springing back, or recovering, to or toward its original unstressed shape or configuration when the stress is removed. The elastic material is preferably highly elastic. The material for the elastic member can be polymeric or metallic, or a combination of both. Such materials include silicone, polyvinyl resins (especially polyvinylchloride), polyethylene, resilient polyacetals, polyurethane, synthetic rubbers, Teflon" tetrafluorethylene fluorocarbon polymer, spring-tempered steel, and spring-tempered stainless steel.

The use of metals, such as shape-memory alloys, for the elastic member is preferred. Shape-memory alloys that exhibit pseudoelasticity, in particular superelasticity, are especially preferred.

U.S. Pat. No. 4,935,068, which is commonly assigned with the present application and incorporated herein by reference, teaches the fundamental principles of shape memory alloys. Some alloys which are capable of transforming between martensitic and austenitic shapes are able to exhibit shape-memory effect. The transformation between phases may be caused by a change in temperature. For example, a shape memory alloy in the martensitic phase begins to transform to the austenitic phase when its temperature raises above $A_s$ and the transformation is complete when the temperature drops below $M_s$ and is complete when the temperature drops below $M_f$. The temperatures $M_s$, $M_f$, $A_s$, and $A_f$ define the thermal transformation hysteresis loop of the shape memory alloy.

Under certain conditions, shape memory alloys exhibit pseudoelasticity, which does not rely on temperature change in order to accomplish shape change. A pseudoelastic alloy is capable of being elastically deformed far beyond the elastic limits of conventional metals.

The property of pseudoelasticity of certain shape-memory alloys, which preferably are used for the elastic member of this invention, is the subject of a paper entitled "An Engineer's Perspective of Pseudoelasticity", by T. W. Duerig and R. Zadno, published in *Engineering Aspects of Shape Memory Alloys*, page 380, T. W. Duerig, K. Melton, D. Stoeckel, and M. Wayman, editors, Butterworth Publishers, 1990 (proceedings of a conference entitled "Engineering Aspects of Shape Memory Alloys", held in Lansing, Mich. in August 1988). As discussed in the paper, the disclosure of which is incorporated herein by reference, certain alloys are capable of exhibiting pseudoelasticity of two types; one type is superelasticity, and the other type is linear pseudoelasticity.

"Superelasticity" arises in appropriately treated alloys while they are in their austenitic phase at a temperature which is greater than $A_s$ and less than $M_d$ ($A_s$ is the temperature at which, when a shape-memory alloy in its martensitic phase is heated, the transformation to the austenitic phase begins, and $M_d$ is the maximum temperature at which the transformation to the martensitic phase can be induced by the application of stress). Superelasticity can be achieved when the alloy is annealed at a temperature which is less than the temperature at which the alloy is fully recrystallized. Alternative methods of creating superelasticity in shape memory alloys, such as solution treating and aging, or alloying, are also discussed in the paper referenced before ("An Engineer's Perspective of Pseudoelasticity"). An elastic member can be provided with a desired configuration by holding it in that configuration during annealing, or during solution treatment and aging. An elastic member formed from an alloy which exhibits superelasticity can be deformed substantially reversibly by 11% or more.

In contrast, "linear pseudoelasticity" is believed not to be accompanied by a phase change (again discussed in the paper entitled "An Engineer's Perspective of Pseudoelasticity"). It is exhibited by shape-memory alloys which have been cold worked or irradiated to stabilize the martensite, but have not been annealed in the manner discussed above. An elastic member formed from an alloy which exhibits linear pseudoelasticity can be deformed substantially reversibly by 4% or more. The treatment of shape memory alloys to enhance their pseudoelastic properties is also discussed in U.S. Pat. No. 4,935,068 to Duerig, the disclosure of which is incorporated herein by reference.

While the alloy that is used in the elastic member 24 may exhibit either linear pseudoelasticity or superelasticity, or pseudoelasticity of an intermediate type, it is generally preferred that it exhibit superelasticity because of the large amount deformation that is available without the onset of plasticity. U.S. Pat. No. 4,665,906 to Jervis, which is commonly assigned with the present application and is incorporated herein by reference, teaches the use of pseudoelastic shape-memory alloys in the medical devices.

The elastic material is selected according to the characteristics desired of the article. For some applications where limited elastic behavior is acceptable (for example, less than 1.5% elastic deformation), conventional spring materials such as titanium, steel, and beryllium copper alloys can be suitable. When a shape-memory alloy is used, it is preferably a nickel titanium based alloy, which can include additional elements which might affect the yield strength that is available from the alloy or the temperature at which particular desired pseudoelastic characteristics are obtained. For example, the alloy can be a binary alloy consisting essentially of nickel and titanium, for example 50.8 atomic percent nickel and 49.2 atomic percent titanium, or it may include a quantity of a third element such as copper, cobalt, vanadium, chromium, or iron. Alloys consisting essentially of nickel, titanium, and vanadium, such as disclosed in U.S. Pat. No. 4,505,767, are preferred for some applications, particularly since they can also exhibit superelastic properties at or around body temperatures, and because they are stiffer and/or can store more elastic energy. Copper based alloys can also be used, for example, alloys consisting essentially of copper, aluminum and nickel, copper, aluminum and zinc, and copper and zinc.

An elastic member exhibiting superelasticity can be substantially reversibly deformed, by as much as eight percent or more. For example, a 1.00 meter length of superelastic wire can be stretched to 1.11 meters in length, wherein the alloy undergoes a phase change to contain more stress-induced martensite. Upon release of the stress, the wire returns substantially to its 1.00 meter length, and its alloy correspondingly returns to contain more austenite. By way of contrast, a similar wire of spring steel or other conventional metal can only be elastically stretched approximately one percent, or to 1.01 meter in length. Any further stretching of the conventional wire, if not resulting in actual breakage of the wire, results in a non-elastic (plastic) transformation such that upon relief of the stress, the wire does not return to its original length. Linear pseudoelastic and superelastic materials can also be bent, twisted, and compressed, rather than stretched, to a far greater degree than any conventional metals.

It is believed that the superelastic property is achieved by phase transformation within the alloy, rather than by the dislocation movements which occur during the plastic deformation of ordinary metals. A superelastic material can be deformed and released thousands of times, without being subject to breakage due to the metal fatigue which limits the number of deformation cycles which an ordinary metal can undergo without failure.

As discussed in detail below with regard to the figures, the cannula 22, the elastic or bending member 24, and the straightener 26 can be oriented in a wide variety of configurations. The straightener can be inside or outside the cannula, or built into the wall of the cannula. Similarly the elastic member 24 can be inside or outside the cannula, or embedded in the wall of the cannula. The elastic member 24 can be hollow and the straightener can be sized to slide into the elastic member. The straightener can be hollow and the elastic member can be sized to slide into and out of the straightener.

The article 20 can include more than one straightener and more than one elastic member 24. For example, a plurality of elongated elastic members can be embedded in or positioned adjoining the wall of the cannula, such as positioned equally spaced apart around the wall of the cannula. For example, if four elastic members 24 are used, they can spaced apart from each other at about 90°. Alternatively, a plurality of elastic members can be used and placed end-to-end rather than having a single elongated elastic member.

In addition the elastic members need not be generally linear in configuration, but rather can be helical or in a "zigzag" configuration. The elastic members need not be parallel to each other, but rather can be twisted together as in a braid.

The amount of bend available from the elastic member can vary with each application, but generally a bend of at least about 20° is desired, with a maximum bend of about 180° being sufficient for most practical applications.

The draw wire 32 can be formed from any number of materials, such as surgical stainless steel or piano wire, that is sufficiently strong to be able to pull on the element to be moved, i.e. the straightener 26 or the elastic member 24, depending on the application. In addition, preferably the draw wire is sufficiently stiff that it can be pushed in the opposite direction for restoring the element moved to its original position. This allows repeated bending and unbending of the distal segment 30 of the cannula 22.

When the elastic member 24 provided at the distal end portion 30 of the cannula 22 is at least partly formed of a superelastic shape-memory alloy, it has elastic strain characteristics capable of being displaced to a comparatively high extent under minimal stress and is easily deformable to a straight configuration. Shape-memory alloys have a special feature which is beneficial for any of the embodiments of this invention. As a superelastic shape-memory alloy is increasingly deformed from its unloaded shape, some of its austenitic phase changes into its stress-induced martensite phase. The stress-strain curve presents a plateau during this phase change. This means that while the alloy undergoes this phase change, it can deform greatly with only minimal increases in loading. Therefore, elastic members comprising superelastic shape-memory alloys have a built-in safety feature. These elastic members can be designed such that when they are loaded beyond a certain amount, the elastic members tend to deform with a concomitant austenite phase to stress-induced martensite phase change, instead of merely presenting a greater resistance with limited deformation to the load, which is seen with conventional metals.

Because superelastic shape-memory allows are easily deformed, when the distal end portion 30 of the cannula 22 goes through a bent portion of a channel, such as a blood vessel, a high flexural deformation value can be obtained under a comparatively low load. This allows the cannula 22 to pass through channels in the mammalian body such as blood vessels because the cannula can be comparatively easily curved according to vascular branching, and the cannula can be smoothly advanced to a predetermined position. A torque can be applied to the cannula to reliably and readily direct the distal portion 30 toward a predetermined position in the path being traversed, so that insertion of the distal segment 30 to a designated position in a complicated system can be achieved.

With reference to FIGS. 1A, 1B and 1C, when the article 20 is an endoscope, the cannula 22 is provided with multiple lumens, a lumen 28A for a fiberoptic element 36, a second lumen 28B for the elastic member 24, and a third lumen 28C for the draw wire 32 and straightener 26. The proximal end of the device is provided with a handle 38 for holding the device 20 and torquing the distal segment 30 of the cannula. For instance, syringe-plunger mechanisms, slider mechanisms, scissors action mechanisms, and pistol grip mechanisms can be utilized. Handle means 38 are provided for moving the draw wire 32 back and forth for correspondingly moving the straightener 26 back and forth axially in the cannula 22, for correspondingly bending and unbending the distal segment 30 of the cannula.

In the drawings discussed below, when the same reference numbers are used as used in earlier figures, the elements are substantially the same and serve substantially the same function, although there may be minor differences.

In all of the embodiments, preferably the elastic members are at least partly made of a superelastic shape-memory alloy.

In the version of the invention shown in FIGS. 2A, 2B, and 2C, a cylindrical, tubular external straightener 37 is provided exterior of the cannula 22. The straightener 37 is concentric with and coaxial with the cannula 22, and is sized so that relative axial movement is possible between the cannula 22 and the straightener 37. Within the lumen 28 of the cannula 22 there is an elastic member 24. By pushing or extruding the cannula 22 out of the straightener 37 (or alternatively pulling the straightener 37 out of the distal segment 30 of the cannula 22), the cannula and the elastic member are transformed from the configuration in FIG. 2A to that of FIG. 2B, thereby achieving a curved configuration. Reversal of this movement results in the cannula reverting to its straight configuration as shown in FIG. 2A from the curved configuration of FIG. 2B.

As shown in FIG. 2D, a plurality of elastic members 24 can be used, and these elastic members can be embedded in the wall of the cannula 22. The elastic members 24 in FIG. 2D extend parallel to the longitudinal axis of the cannula 22 and optionally are equally spaced apart from each other around the diameter of the cannula, being about 90° apart from each other. An advantage of using more than one bending element 24 as shown in FIG. 2D is that more bending force can be achieved, particularly when the bending elements 24 are oriented so that they all tend to bend in the same direction.

As shown in FIGS. 2A and 2B, it is not necessary that the entire straightener element 37 be stiff. In the version of FIG. 2, the actual portion of the straightener 37 that is stiff is only an and segment 37A, since this is the only portion of the straightener 37 that serves to prevent bending. The proximal portion 39 of the straightener 37 is sufficiently flexible to be bent. In an alternate version of this embodiment, the tubular straightener 37 is axially slidable within the lumen 28.

In the version of the invention shown in FIGS. 3A and 3B, a tubular hollow straightener 40 is used and the straightener is sized to slide over the elastic member 24 and is composed at least partly of a superelastic shape-memory alloy. This sliding movement stresses the alloy into a state or phase containing more stressed-induced martensite in which state the elastic member 24 is substantially straight. By pulling on a wire 32 in the direction shown by arrow 42 in FIG. 3A, the straightener 40 is pulled at least partly off the elastic member 24 to the position shown in FIG. 3B. This results in the alloy transforming to its austenitic state or phase containing less martensite and more austenite, in which state the memory alloy element is in its bent shape, thereby resulting in the distal segment 30 of the cannula 22 bending as shown in FIG. 3B. The amount the straightener 38 is moved in the direction shown by arrow 42 determines the amount of curvature achieved. Pushing on the draw wire 32 in the direction shown by arrow 44 in FIG. 3B results in the straightener 38 sliding over the superelastic shape-memory alloy elastic member 24, thereby increasing the martensite content of the alloy, which serves to transform the device 20 into the configuration shown in FIG. 3A.

In the version of the invention shown in FIGS. 4A and 4B, the elastic member 46 is a hollow tube with a lumen 47 that is optionally capped. A straightener or stressing member 48 is sized to fit within the lumen 47 of the elastic member 46. The elastic member 46 is at the distal segment 30 of the cannula 22. Sliding the straightener 48 out of the lumen 47 of the elastic member 46 in the direction shown by arrow 42 results in the distal segment 30 of the cannula 22 bending as shown in FIG. 4B. The amount that the straightener 48 is slid out of the lumen 47 controls the degree of curvature achieved. As shown in FIG. 4B, only partially withdrawing the straightener 48 results in a relatively small amount of curvature of the distal segment 30. Complete withdrawal of the straightener 48 results in a greater amount of curvature.

Sliding the straightener 48 back into the lumen 47 of the elastic member 46 in the direction shown by arrow 44 in FIG. 4B reverts the cannula 22 and the elastic member 46 to the substantially straight linear configuration shown in FIG. 4A. This is achieved by reversion of the superelastic shape-memory alloy that is used to at least partly form the elastic member 24 to its stress-induced martensitic state from its austenitic state.

In FIGS. 5A and 5B, the cannula 22 is provided with a tubular, elongated straightener 50 having a lumen 51, the longitudinal axis of the straightener 50 being substantially parallel to the longitudinal axis of the cannula 22. The straightener 50 is positioned upstream of, but proximate to the distal segment 30. An elastic member 52 is sized to fit within the lumen 51 of the straightener 50 and be stressed thereby, and is adapted to be slid axially within the lumen 28 of the cannula 22 and the lumen 51 of the stiffener 50 by being maneuvered with a draw wire 32.

The elastic member 52 is preferably formed of a superelastic shape-memory alloy, the alloy displaying reversible stress-induced martensite at about body temperature such that it has a stress-induced martensitic state having relatively more martensite phase and an The elastic member is substantially straight in its constrained stress-induced martensitic state, and has the curved configuration as shown in FIG. 5B when the alloy is in its unconstrained austenitic state.

The distal segment 30 of the cannula 22 is transformed from its straight configuration of FIG. 5A to its curved configuration of FIG. 5B by sliding the elastic member 52 in the direction of arrow 44 in FIG. 5A out of the straightener 50 into the distal segment 30 of the cannula. The distal segment 30 is straightened from the position shown in FIG. 5B to the substantially straight configuration of FIG. 5A by pulling the elastic member 52 back into the straightener 50 in the direction shown by arrow 42 in FIG. 5B. This transforms the alloy to its stress-induced martensitic state, in which the elastic member 52 is substantially straight, and at the same time the straightener 50 is sufficiently stiff to overcome any bending moment present in the elastic member 52.

The version shown in FIGS. 5A and 5B is similar to the version shown in FIGS. 3A and 3B. A key difference is that in the version of FIGS. 3A and 3B, the straightener 40 is moved while the elastic member is stationary relative to the cannula 22; in the version of FIGS. 5A and 5B, the straightener 50 is stationary relative to the cannula and the elastic member 52 moves.

The versions of the invention depicted in FIGS. 6A, 6B, 7A and 7B are very similar to the version shown in FIGS. 4A and 4B. A significant difference is the change in the configuration of the elastic member. In the version shown in FIGS. 4A and 4B, the elastic member 46 is a tube with a closed end. In FIG. 6 the elastic member is in the shape of a generally right circular cylindrical halix member 60. In the version of FIGS. 7A and 7B, the elastic member 61 is in the form of a "zigzag" configuration. In both versions, the elastic member is substantially coaxial with the cannula 22.

In the version shown in FIGS. 8A and 8B, a rod-like straightener 64 is provided upstream of the distal portion 30 of the cannula 22, on the proximate side of the distal segment 30 within the lumen 28 of the cannula 22. An elastic member 66 is sized to slide over the straightener 64, the elastic member 66 being tubular and having a lumen 68 sized to accommodate the straightener 64. The elastic member 66 can be pulled onto the straightener 64 and off the straightener 64 into the distal segment 30 of the cannula 22 with the draw wire 32. Thus the version of the invention shown in FIGS. 8A and 8B is similar to the version of the invention shown in FIGS. 4A and 4B. A difference is that in the version of FIGS. 4A and 4B, the straightener 50 is a cylindrical tube with the elastic member 52 slidable into the tube; in the version of FIGS. 8A and 8B, the elastic member 66 is tubular while the straightener 64 is sized so that the straightener 64 can slide into the elastic member 66.

When the elastic member 66 is on the straightener 64, the straightener 64 keeps the elastic member straight, thereby keeping the cannula 22 straight. By moving the elastic member 66 in the direction of arrow 44 as shown in FIG. 8A into the distal segment 30, the elastic member moves toward its unconstrained configuration, wherein the elastic member 66 bends and causes the distal segment 30 to likewise bend, as shown in FIG. 8B. The device 20 can be reverted to the original configuration of FIG. 8A from that of FIG. 8B by sliding the elastic member 66 back onto the straightener 64 in the direction shown by arrow 42 in FIG. 8B.

In FIGS. 5A and 8A, the stiffener and the elastic member are both proximal to the distal segment 30 rather than being located in the distal segment. This may be advantageous in certain situations, since the cannula distal segment 30 by itself preferably is flexible and pliant, so that when the stiffener and the elastic member are both proximal to the distal segment 30, the cannula 22 has a relatively atraumatic leading distal segment 30.

In the version of the invention shown in FIGS. 9A and 9B, the cannula 22 has an elongated elastic member 24 in its distal segment 30. The elastic member 24 is formed at least partly from a superelastic shape-memory alloy. The alloy displays reversible stressed-induced martensite at about body temperature such that it has a stress-induced martensitic state (containing relatively more martensite) and an austenitic state (containing relatively more austenite). The elastic member 24 is in a substantially straight shape when the alloy is in its stressed-induced martensitic state, and the elastic member is in a bent shape when the alloy is in its austenitic state. The elastic member, which is on the inside wall 70 of the cannula 22 and has a longitudinal axis parallel to the longitudinal axis of the cannula, includes a short lever arm 74 extending radially inwardly at the distal end of the elastic member. Secured to the lever arm 74 is the draw wire 32, which serves to stress the elastic member 24. Tensioning of the draw wire 32 by pulling on it in the direction of arrow 42 draw wire 32 by pulling on it in the direction of arrow 42 in FIG. 9A results in the alloy of the elastic member 24 being transformed to its stress-induced martensitic state, with the result that the elastic member 24 is substantially straight as shown in FIG. 9A. This results in the distal segment of the cannula likewise being substantially straight.

Release of the tension on the draw wire 32 transforms the alloy of the elastic member 24 to its austenitic state, with the result that the elastic member reverts to its bent shape, which results in the distal segment 30 of the cannula 20 likewise becoming bent. This configuration of the device is shown in FIG. 9B. Because the alloy displays reversible stressed-induced martensite behavior at about body temperature, alternately tensioning and releasing the draw wire 32 alternately straightens and bends the distal segment 30 of the cannula 22.

The versions of a device according to the present invention shown in FIGS. 10A/10B and 11A/11B are substantially the same in concept and operation as the device shown in FIG. 9A/9B. The only significant difference is the change in the configuration of the elastic member in the distal segment 30 of the cannula. In the version shown in FIGS. 9A and 9B, the elastic member 24 is a rod. In the version shown in FIGS. 10A and 10B, the elastic member is in the shape of a generally right circular cylindrical helix member 60 (as shown in FIG. 6). In the version of FIGS. 11A and 11B, again the elastic member is in the form of a helix, but not right circular cylindrical, but rather of a "zigzag" configuration (as shown in FIG. 7). In both versions of FIGS. 10 and 11, the helix is substantially coaxial with the cannula 22.

In the versions of the invention shown in FIGS. 9, 10, and 11, the elastic member is bent along its longitudinal axis in its unconstrained configuration. However, in any of these versions, the elastic member can be straight along its longitudinal axis in its unconstrained configuration, and the draw wire 32 could be used to bend the elastic member and thereby bend the distal segment 30.

The device 20 shown in FIG. 12 has an internal lumen with a distal portion 84 of relatively large diameter and an adjoining proximal portion 86 of relatively small diameter. This is accomplished by providing a cannula 22, which has a lumen 28 of substantially constant internal diameter, with a hollow plug 90 therein, the hollow plug 90 having a lumen 91 of relatively smaller diameter. The cannula 22 and the plug 91 are coaxial, with the plug 91 being located in the proximal portion 86 of the device 20. Rather than providing the device 20 as two separate elements, namely the cannula 22 and the plug 90, a single integral structure can be used.

The distal portion 30 of the cannula 22 is sufficiently flexible to be bent. An elongated elastic member 98 is sized to fit within the lumen of the plug 90 and is located therein, and is axially slidable in the plug 90 into the open distal portion 30 of the cannula 22. The elongated elastic member 98 comprises two elongated substantially parallel segments 98A connected to each other at their distal ends 99. Preferably the elastic member 98 is at least partly formed from a superelastic alloy displaying reversible stressed-induced martensite at about body temperature.

FIGS. 12A-1 and 12A-2 show curved distal ends 105 of the elastic segments 98A forming a loop when they are out of the plug and are completely in the distal portion 84 of the lumen, and are front and side views, respectively. FIGS. 12B-1 and 12B-2 show the curved parts 105 of the elastic segments 98A partially withdrawn into the proximal portion 86 of the lumen, and are front and side views, respectively.

The elastic member 98 is stressed by being withdrawn into the proximal portion 86 in the direction indicated by arrow 42. The stress on the curved parts 105 is such that the segments 98A tend to fold at point 99 and twist axially in the lumen. In other words, the curved parts 105 collapse toward each other by folding out of plane, rather than bending toward each other exclusively in their plane. Therefore, the distal portion 84 of the cannula 22 also bends. The direction of bend can be controlled by making the curved parts 105 join slightly out of plane at point 99.

This version of the invention has the advantage that the entire cannula 22 can be flexible, since there is no need for a stiffener. Moving the elastic member 98 in the direction indicated by arrow 44 permits the elastic members to return toward their unconstrained substantially planar configuration, which tends to return to the distal segment 84 toward its straight configuration.

FIG. 13 shows another device 110 embodying slightly different features of this invention. Two elastic members 111 are housed in parallel lumens 28 of a cannula 22. The portions of elastic members 111 which are housed within the distal segment 30 of the cannula are curved, but when the elastic members 111 are constrained within the lumens 28, they are positioned to tend to curve in opposite directions. If the elastic members 111 are identically curved and of the same elastic material (preferably superelastic shape-memory alloy), each applies a force opposite to the other, with the net effect that they keep the distal segment 30 straight. However, because the lumens 28 permit rotation of the elastic members 111 therein, then these elastic members can be rotated together, or in unison, to bend the distal segment 30. In this manner, the distal segment 30 can be bent in any desired direction without turning the entire cannula 22, merely by rotating the elastic members. Furthermore, no stiffener is needed so that the entire cannula 22 is relatively flexible.

Some patterns of bend, viewed diagrammatically from the distal end of cannula 22, are shown in FIGS. 13B-13I. Version 1 of each of FIGS. 13B-13I, i.e., FIG. 13D-1, is a top schematic view of the device 110, with an arrow 119 showing the net effective direction of bending moment resulting from the combined bending moment of the two elastic members 111. Version 2 of each figure, i.e., FIG. 13D-2, shows the direction of the bending moment exerted by each of the elastic members, which combined bending moment results in the bending shown by arrow 119. Thus in FIG. 13D, the distal segment 30 bends to the right as seen in the view of FIG. 13D, and as shown by arrow 119.

Alternative variations of this version are available. For example, more than two elastic members can be utilized. Also, elastic elements of different inherent elasticities and curvatures can be used. For instance, one of the elastic members 111 of FIG. 13 can be replaced by two separate thinner and/or weaker elastic elements to incorporate a bias to bend in a set direction into the device 110.

Another version of a steerable cannula 130 is shown in FIG. 14. In the embodiment, multiple elastic members 132 are at the distal end 134 of the cannula 130, but not in the distal segment 136. Each of the elastic members 132 is curved in its unconstrained shape, but when stored within the cannula, as shown in FIG. 14A, they are positioned such that they tend to curve in diverging directions. When one of the elastic members is slid distally into the distal segment 136, it causes the distal segment to curve in the direction of curvature of this elastic member, as shown in FIG. 14B. FIG. 14A arbitrarily shows four elastic members, but any number of elastic members greater than or equal to two could be used. When two or more elastic members are slid distally into distal segment 136, then the resultant curvature of distal segment 136 is in the same direction as the resultant of the combined force vectors of the elastic members which have been slid distally into distal segment 136.

FIG. 14C schematically shows end-on views of the various directions of curvature in the case of four elastic members, where + marks an elastic member which has been slid distally into the distal segment 136, * marks an elastic member which has not been slid distally into distal segment 136, and the open arrow 137 shows the direction of curvature.

An alternative version of the embodiment shown in FIG. 14 can have multiple elastic members already present in the distal segment 132 of the cannula. Sliding one or more elastic members in a proximal direction out of the distal segment 136 would then permit the remaining elastic elements to bend the distal segment 136 in the same direction as the resultant vector of all the forces in the remaining elastic members.

In the embodiment of FIG. 14, the elastic members can be positioned such that their concave surfaces face radially inward when they are not constrained, or they can be positioned such that their concave surfaces face radially inward when they are not constrained. Also, segment 138 can be reinforced so that no bending can occur in this segment no matter how many elastic elements have been moved to achieve curvature of distal segment 136.

With reference to FIGS. 15A, 15B, and 15C, the device 20 in accordance with the version of the invention shown in FIG. 2A is presented as navigating a portion of a tortuous path in a human body. As shown in FIG. 15A, the device is substantially straight and has reached a branch in the path 172 where the device can either go through a first branch 174 or a second branch 176. To cause the device 20 to traverse the second branch 176, the straightener 26 is caused to axially slide proximately to uncover the distal segment 30 of the cannula 22, resulting in the distal segment 30 bending toward the second branch 176, as shown in FIG. 15B. Then the entire device can be pushed in the direction of the distal segment into the second branch 176, as shown in FIG. 15C. In contrast, if it is desired to enter the first branch 174, the entire device or the bending mechanism itself can be rotated along its axis by 180°. The same sequence of withdrawing the stiffener 20 to uncover the distal segment 30 to permit this segment to bend toward the first branch 174, and then advancing device 20 can then be carried out.

Most of the embodiments described so far for this invention only permit bending in one plane. If desired, more than one bending mechanism (e.g., multiple elastic member/straightener combinations) can be incorporated into an endoscopic device or catheter to permit bending in more than one plane. For example, referring to FIG. 1, if straightener 26 has a strip shape, with the strip being in a plane which includes elastic member 24, then straightener 26 can be used to prevent elastic member 24 from bending distal segment 30, but permits bending of distal segment 30 in a second plane different from the first plane (which includes elastic member 24 and straightener 26). Therefore, a second mechanism (which includes a second straightener, a second draw wire, and a second elastic member) can be incorporated in a device which is in a second plane (preferably perpendicular) different from the first plane and which permits bending of distal of distal segment 30 in a direction out of the first plane.

Although the present invention has been described in considerable detail with reference to certain preferred versions thereof, other versions are possible. Therefore, the scope of the appended claims should not be limited to the description of the preferred versions of the invention described above.

What is claimed is:

1. An article of manufacture comprising:
   (a) an elongated tube having an internal lumen, a peripheral wall, and including a hollow, bendable distal segment;
   (b) an elastic member engaging the distal segment of the tube, the elastic member having (i) a bent shape and (ii) a substantially straight shape, the elastic member being sufficiently stiff to cause the distal segment to bend when the elastic member is in its bent shape; and
   (c) straightening means capable of preventing the elastic member from bending;
   wherein the straightening means and the elastic member are capable of relative axial movement, and wherein such relative axial movement disengages at least part of the elastic member from the straightening means, thereby transforming the elastic member from one shape to another for correspondingly bending or unbending the distal segment of the tube.

2. The article of claim 1 wherein the elastic member is a memory alloy element formed at least partly from a superelastic shape-memory alloy, the alloy displaying reversible stress-induced martensite at about body temperature such that it has a stress-induced martensitic state containing relatively more martensite and an austenitic state containing relatively more austenite, the memory alloy element being in its bent shape when the alloy is in its stress-induced martensitic state, and wherein the straightening means is capable of transforming the elastic member to and from its stress-induced martensitic state.

3. The article of claim 1 wherein the elastic member is a memory alloy element formed at least partly from a superelastic shape-memory alloy, the alloy displaying reversible stress-induced martensite at about body temperature such that it has a stress-induced martensitic state and an austenitic state, the memory alloy element being in its substantially straight shape when the alloy is in its stress-induced martensitic state, and wherein the straightening means is capable of transforming the elastic member to and from its stress-induced martensitic state.

4. The article of claim 1 in which the elastic member is inside the lumen of the tube.

5. An article of manufacture comprising:
   (a) an elongated tube having an internal lumen, a peripheral wall, and including a hollow, bendable distal segment;
   (b) an elastic member positioned inside the lumen of the tube and engaging the distal segment of the tube, the elastic member having (i) a bent shape and (ii) a substantially straight shape, the elastic member being sufficiently stiff to cause the distal segment to bend when the elastic member is in its bent shape
   (c) straightening means capable of preventing the elastic member from bending which is tubular and around elastic member.
   wherein the straightening means and the elastic member are capable of relative axial movement, and wherein such relative axial movement transforms the elastic member from one shape to another for correspondingly bending or unbending the distal segment of the tube.

6. The article of claim 1 sized for insertion into a mammalian body.

7. The article of claim 6 wherein the tube has multiple lumens.

8. The article of claim 7, wherein a first lumen is provided for a fiberoptic element, a second lumen is provided for the elastic member, and Dan a third lumen is provided for the straightening means, the tube thereby being adapted to be used as an endoscope.

9. The article of claim 1 in which the stiffening means is within the lumen of the tube.

10. The article of claim 1 in which the elastic member directly contacts the tube.

11. The article of claim 1 in which the straightening means directly contacts the elastic tube.

12. The article of claim 1, 2, or 3 in which the elastic member transforms from one shape to another without application of heat.

13. A device suitable for insertion into a mammalian body comprising:
   (a) a cannula having an internal lumen, a peripheral wall, and a hollow, bendable distal segment;
   (b) an elastic member inside the cannula and axially slidable therein between a first position proximate to the distal segment and a second position remote from the distal segment, the elastic member having a bent shape and being sufficiently stiff to cause the distal segment to bend when the elastic member is in its bent shape, the elastic member being capable of being deformed into a substantially straight shape;
   (c) a tubular, substantially straight stiffener within the cannula, the straightener having an internal lumen sized to receive the elastic member, the straightener being located remote from the distal segment of the cannula and being sufficiently stiff to transform the elastic member to its substantially straight shape; and
   (d) means for moving the elastic member axially in the cannula between its first and second position, the elastic member in its first position bending the distal segment of the cannula and in its second position being within the straightener and thus substantially straight, thereby correspondingly bending and unbending the distal segment of the cannula.

14. A method for navigating a tortuous path comprising the steps of:
   (a) selecting the article claimed in claim 1;
   (b) inserting the article into the tortuous path, the distal segment of the tube being inserted first; and
   (c) causing relative axial movement between the straightening means and the elastic member for transforming the elastic member from one shape to another for correspondingly bending or unbending the distal segment of the tube.

15. The method of claim 14 wherein the tortuous path is in a mammalian body.

16. A method for navigating a tortuous path in a mammalian body comprising the steps of:
   (a) selecting the device claimed in claim 13;
   (b) inserting the device into the mammalian body, the distal segment of the cannula being inserted first; and
   (c) moving the cannula from its first position to its second position for transforming the distal segment of the cannula to a bent shape.

* * * * *

UNITED STATES PATENT AND TRADEMARK OFFICE
CERTIFICATE OF CORRECTION

PATENT NO. : 5,231,989
DATED : August 3, 1993
INVENTOR(S) : Middleman et al.

It is certified that error appears in the above-indentified patent and that said Letters Patent is hereby corrected as shown below:

Column, 2, line 43, replace "decreases" by --increases--.

Column 10, line 31, replace "allows" by --alloys--.

Column 11, line 31, replace "and" by --end--.

Column 12, line 15, replace "form" by --from--.

Column 12, line 32, insert after "an" --unstressed state having relatively more austenitic phase--.

Signed and Sealed this

Twenty-third Day of August, 1994

Attest:

BRUCE LEHMAN

Attesting Officer
Commissioner of Patents and Trademarks